(12) United States Patent
Kaupp

(10) Patent No.: US 6,603,540 B1
(45) Date of Patent: Aug. 5, 2003

(54) METHOD FOR EXAMINING ROTATIONALLY SYMMETRICAL OBJECTS

(75) Inventor: Ansgar Kaupp, Ahrensburg (DE)

(73) Assignee: Basler, AG, Ahrensburg (DE)

( * ) Notice: Subject to any disclaimer, the term of this patent is extended or adjusted under 35 U.S.C. 154(b) by 0 days.

(21) Appl. No.: 09/497,826

(22) Filed: Feb. 3, 2000

(30) Foreign Application Priority Data

Feb. 4, 1999 (DE) .......................................... 199 04 427

(51) Int. Cl.$^7$ ............................................... G01N 21/00
(52) U.S. Cl. ................ 356/237.1; 356/430; 250/559.45
(58) Field of Search .......................... 356/237.1, 237.2, 356/237.3, 237.4, 237.5, 394, 239.1, 239.3, 239.7, 239.8, 430, 431; 250/559.42, 559.45; 369/53.16, 53.15

(56) References Cited

U.S. PATENT DOCUMENTS

| | | | | |
|---|---|---|---|---|
| 4,423,331 A | * | 12/1983 | Koizumi et al. | 250/559.45 |
| 4,477,890 A | | 10/1984 | Mooney et al. | 369/53 |
| 4,508,450 A | * | 4/1985 | Ohshima et al. | 356/237.2 |
| 4,794,265 A | * | 12/1988 | Quackenbos et al. | 250/559.45 |
| 4,954,723 A | * | 9/1990 | Takahashi et al. | 250/559.18 |
| 5,031,112 A | * | 7/1991 | Sakai et al. | 702/40 |
| 5,648,850 A | | 7/1997 | Basler et al. | 356/369 |
| 5,729,520 A | | 3/1998 | Klicker | 369/112 |
| 5,760,907 A | | 6/1998 | Basler et al. | 356/390 |
| 5,914,495 A | * | 6/1999 | Ishizuka et al. | 250/559.45 |
| 5,917,933 A | | 6/1999 | Klicker | 382/149 |
| 6,483,789 B1 | * | 11/2002 | Kubota et al. | 369/53.16 |
| 2001/0015415 A1 | * | 8/2001 | Okamoto | 250/559.45 |

FOREIGN PATENT DOCUMENTS

| | | | | |
|---|---|---|---|---|
| DE | 4434474 A1 | * | 3/1996 | G01M/11/02 |
| DE | 4434475 A1 | * | 3/1996 | G01N/21/88 |
| WO | WO 97/20312 | | 6/1997 | |

OTHER PUBLICATIONS

Patent Abstracts of Japan, One page English language Abstract of Japanese Publication No. 63067550.

* cited by examiner

*Primary Examiner*—Hoa Q. Pham
(74) *Attorney, Agent, or Firm*—Howson and Howson

(57) ABSTRACT

The invention pertains to a method for examining a series of objects that are symmetrical in reference to a rotational axis, e.g., circular disks, during or after the manufacturing process of the disks. In particular, the invention pertains to the optical examination of circular data carriers, e.g., CD, DVDs, CD-Rs or the like. The invention proposes that each object contains at least one marking or is provided with at least one marking. The marking makes it possible to unequivocally determine the angular position of each object about the rotational axis in reference to the marking for objects manufactured in the same manufacturing process. At least one section of the objects is scanned by at least one scanning element, and the marking is detected during the examination process. The scanning result and/or examination result of geometric regions with corresponding positions on the objects in reference to the marking is determined and/or evaluated and/or displayed on a display element in the same angular position in reference to the marking. A defect that always occurs at the same position will always have the same geometric data independent of the rotation of the object to be examined during its transport to the examination point and can be treated with other criteria.

11 Claims, 1 Drawing Sheet

METHOD FOR EXAMINING ROTATIONALLY SYMMETRICAL OBJECTS

FIELD OF THE INVENTION

The invention pertains to a method for examining a series of objects that are symmetrical in reference to a rotational axis, e.g., circular disks. The invention pertains, in particular, to the optical examination of circular data carriers, e.g., CDs, DVDs, CD-Rs and the like. Although the following description primarily pertains to one of these data carriers, the invention is not limited to objects of this type.

BACKGROUND OF THE INVENTION

It is known to carry out a 100% examination of optical data carriers during or after the manufacturing process of the optical data carriers. When examining CDs, CD-Rs or DVDs, optical methods are utilized in which the objects to be examined are turned about their rotational axis and scanned. The surface to be examined, e.g., the flat side having a data area, is scanned and examined with respect to possible defects. Methods of this type are, for example, known from DE 44 34 473 A1, DE 44 34 474 A1 and DE 44 34 475 A1. WO 97/20312 describes a method in which a circular object is always aligned in the same angular position with reference to a marking provided and illustrated on the object.

The illustration of the examined sections of the object usually takes place on a monitor of a data processing system, in which the optical scanning is evaluated. The illustration may be in the form of tables and coordinate data and/or in the form of a pictorial representation of the object to be examined, in which possible defects are distinguished or made visible.

The examination of the objects can be carried out at an arbitrary time during the production, namely after one of the production steps, with said examination frequently being carried out at the end of the manufacturing process, i.e., at the end of the production line. On its transport to the examination station, the object to be examined is subjected to several non-reproducible rotations about its rotational axis, e.g., when lacquering, handling or examining the object. However, this has the disadvantage that, in particular, defects which are produced during essential manufacturing steps and always occur at the same position are not always recognized as such, namely because these defects occur at the same radial distance from the rotational axis, but in different angular positions due to the undefinable rotation, to which the object to be examined is subjected before it reaches the examination station.

In the manufacture of a CD, CD-R or DVD, the essential manufacturing step is the pressing of the blank in the stamper. A defect in the stamper may cause the entire production to result in refuse. Consequently, it would be desirable to rapidly recognize such system defects so as to correspondingly manipulate the ongoing production process, analyze the defect and, if so required, exchange the stamper.

OBJECT OF THE INVENTION

The invention is based on the objective of developing an examination method of the initially mentioned type in such a way that defects can be detected with respect to the rotating direction as well as being classified and corrected.

SUMMARY OF THE INVENTION

According to the invention, this objective is attained due to the fact that preferably each object contains at least one marking or is provided with at least one marking. The marking makes it possible to unequivocally determine the angular position of each object about the rotational axis with reference to the marking for objects manufactured in the same manufacturing process. At least one section of each of the objects is scanned by at least one scanning element and the marking is detected during the examination process. The scanning result and/or examination result of the geometric regions with corresponding positions on the objects relative to the marking is determined and/or evaluated and/or displayed on a display element in the same angular position relative to the marking. The evaluation means evaluating the defects of the respective objects have the same or at least approximately the same position relative to the angular position of the marking and the same radial distance from the rotational axis with other criteria than stochastically occurring defects. Consequently, a defect that always occurs at the same position will always have the same geometric data up to the examination station independent of the rotation of the object to be examined. It is quite obvious that this makes it possible to recognize and classify possible system defects, in particular, defects in the stamper. The determination, evaluation and/or illustration of an otherwise rotationally symmetrical object which is based on the rotating direction makes it possible to rapidly and reliably classify such continuously occurring defects as stamper defects. The defect classification, namely the question whether such a defect results in refuse or not, can be correspondingly optimized.

It is, in principle, practical to carry out the examination in an ongoing production process. This production process can, if so required, be stopped if a system defect is detected.

The examination may also take place in batches for a predetermined number of objects. In this case, either part of or the entire non-rotationally symmetrical imprint may, for example, be used as the marking. This marking or part of the marking can be measured for the alignment based on the rotating direction such that the examination of the objects, in particular, the imprint, is simplified.

It is practical that the marking always has the same position on the display element so as to always illustrate the object in the same alignment. This provides the advantage that the recognition of a defect that always occurs at the same position of the object is significantly simplified. During the determination, evaluation and/or illustration of a geometric point or region of the object by means of coordinates, in particular, polar coordinates or Cartesian coordinates, it is also possible for the marking to form a fixed reference point of the coordinates. This can be realized by means of a corresponding coordinate transformation that can be easily carried out. Due to this measure, each position has the same coordinates referred to the marking, with an identical defect on each object to be examined consequently also having the same coordinates, i.e., such a defect can be rapidly recognized and classified as a system defect.

In this case, it is, in principle, advantageous to provide detection means that determine the defects of the respective objects which have the same position referred to the angular position of the marking and the same radial distance from the rotational axis, with said detection means storing these defects in a memory if so required and counting the defects with the aid of a counting device. Once a predetermined number of identical defects with the same or at least approximately the same position on the objects is exceeded, a signal, e.g., a special message, can be triggered. Due to this measure, an automated determination, classification and display of a system defect can be realized, in particular if the uniformity of the defects is examined and recognized. It is also possible to trigger a signal which stops the production line once a system defect that results in refuse is determined and recognized.

This means that one is able to proceed in such a way that the defects with the positional data and the defect data of at least a predetermined number of already examined objects are stored. The memory may be realized in the form of a shift register or ring memory, in which the values of the oldest examined data carrier are replaced with the values of the data carrier examined last. The number may, for example, lie at 100, 200 or more. The above-mentioned defect recognition in connection with the positional data of the defect makes it possible to generate a signal, i.e., usually a defect signal or a special alarm signal, as an indication for a system defect if a predetermined number, e.g., 10 or 20, of successive data carriers contain similar or corresponding defects at the same position. The defective data carriers do not necessarily have to be manufactured in immediate succession. It is also possible to generate a signal if a predetermined portion of the data carriers examined last contains similar or identical defects at corresponding positions. In this case, the quantity of examined data carriers which is decisive for this process may be smaller than the quantity of the data carriers, for which data are stored in the memory. However, the entire quantity may, in principle, be used as a basis for the rating process. In this case, it is also possible to examine all stored values of the previously examined data carriers with respect to exactly this specific defect once a possible system defect is detected.

It is, in particular, possible that defects which do not result in refuse in individual instances but always occur at the same position of the respective objects can still cause a corresponding signal to be generated, e.g., a message, so as to warn of the risk of a system defect, in particular, a defect in the stamper. This allows a more accurate examination of the objects for possible system defects during the production process, i.e., corresponding manipulations in the production line can be carried out in a timely fashion.

According to another embodiment of the invention, detection means are provided which make it possible to determine that defects always occur at the same position of the respective objects. In this case, this position can be declared as defect-free such that harmless system defects which were detected do not result in refuse. In this case, it may be practical to continue monitoring these determined positions which were initially declared to be defect-free so as to generate a corresponding defect signal if the defect changes, e.g., with respect to its size. These positions which are declared to be defect-free are limited in the rotating direction as well as in the radial direction, i.e., defects on the same radius of another angular position can, for example, still be detected. This means that the reliability of the examination is increased.

The arrangement of the marking is, in principle, arbitrary as long as the marking makes it possible to define an unequivocal angular position. With respect to a data carrier, it is practical to arrange the marking outside of the data area. For example, the marking may be arranged on the outer edge of a circular disk, with the marking being arranged on the outer edge and/or the inner edge on a circular disk with a central hole, e.g., a CD, DVD or CD-R.

In addition, the shape and quantity of the markings is arbitrary as long as an unequivocal determination of the angular position is possible. The marking may, in principle, be realized in the form of a straight line that extends in the radial direction over at least part of the disk. According to one preferred embodiment, the marking forms part of the ID code or consists of the ID code when examining a coded data carrier, e.g., a CD, DVD or CD-R. In this case, one advantageously utilizes the fact that this ID code is always provided on a CD. This means that no separate marking needs to be provided. However, a particular advantage can be seen in the fact that the ID code is applied by the stampers during the pressing of the blank, i.e., the blank can always be measured in an unequivocal angular position referred to the stamper. Consequently, a possible defect of the stamper can be rapidly and reliably detected and classified as a system defect.

It is, in principle, also possible to apply an additional marking while pressing the blank in the stamper during the manufacture of a CD, DVD, CD-R or another similarly designed data carrier. This provides the advantage of simplifying the detection of the now precisely defined marking.

However, it is also possible to apply the marking after the pressing of the blank during the manufacture of a CD, DVD, CD-R or a similarly designed data carrier, namely such that the angular position of the blank referred to its angular position in the stamper can be unequivocally defined. In this case, it is advantageous if the marking is applied onto the object in a removable fashion.

It is quite apparent that the method according to the invention makes it possible to easily detect possible system defects. It is also possible, in particular, during the manufacture of pressed objects, to detect defects in the stampers because such a defect always leads to the same defect at the same position. Without a marking and its detection, it would not be possible to measure and illustrate the object to be examined always in the same angular position so as to evaluate identical defects in the same fashion and/or with identical coordinates or corresponding data. Due to the invention, an evaluation and an illustration can always be achieved in the same angular position referring to a starting position. Consequently, the result of the examination can be more confidently accepted. The invention, in particular, also makes it possible to detect defects in the stampers which would not result in refuse in individual instances during the manufacture of optical data carriers. In this case, the sensitivity of the examination method can be increased if such defects always occur at the same position, i.e., the production process can be manipulated in a timely fashion.

BRIEF DESCRIPTION OF THE DRAWINGS

The invention is described below with reference to the schematic figure, FIG. 1, which shows a top plan view of a CD.

DETAILED DESCRIPTION OF THE PREFERRED METHOD AND DEVICE

Figure 1:
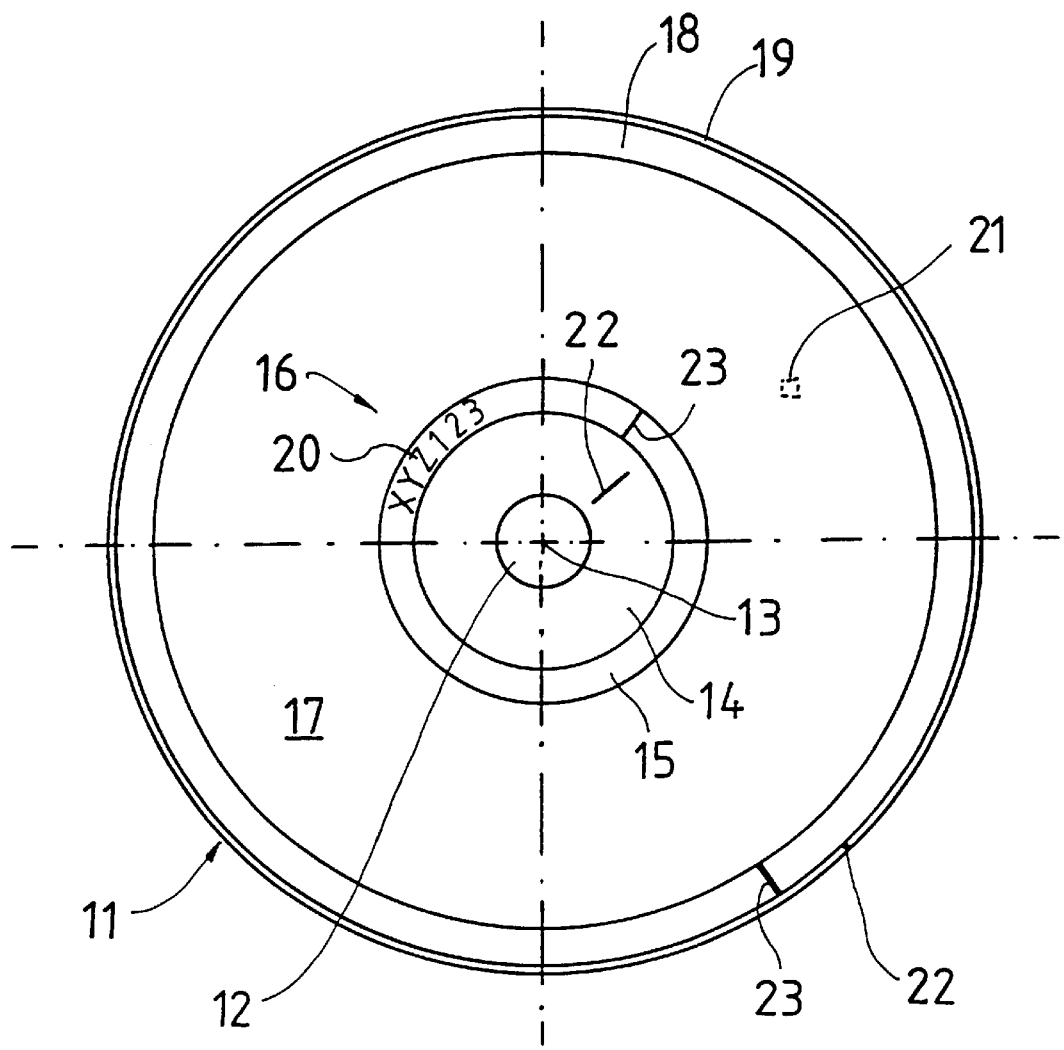

The Compact Disk (CD) 11 shown in the figure is conventionally realized in the form of a circular disk with a central hole 12. This means that the CD is entirely symmetrical in reference to the rotational axis 13. The central hole 12 is usually bordered by an inner coaxial edge region 14 for holding the CD in the corresponding player. A coaxial region 15 that contains the identification code, namely the ID code 16, is situated adjacent to the aforementioned edge region. This coaxial region 15 is surrounded by the data area 17. Depending on the data quantity, a lead-out 18 or the outer edge region 19 is situated adjacent to the data area.

It is quite apparent that such a CD, in particular, the data area 17, always appears identical to an optical scanning element of an examination device independently of the rotation if no additional measures are provided. This is the reason why defects which, for example, always occur at the same position referred to the radial distance and the angular position due to a defective stamper used in the pressing process can, in principle, not be detected and classified as such.

An orientation of the CD in the rotating direction can only be attained with markings that are not symmetric in the rotating direction. For example, the ID code 16 in the form of a combination of numerals and letters is not symmetrical in the rotating direction. The ID code may also contain a bar code or another pictorial coding that is also not circularly symmetrical. Consequently, it is possible to select an arbitrary symbol 20 or the beginning or the end of the ID code as the marking. This marking makes it possible to define a certain geometric region 21 in a defined angular position about the rotational axis 13 referring to the marking as well as at a corresponding distance from the rotational axis.

Due to this measure, it is possible to determine and evaluate identical regions with identical data, in particular, coordinates, for all objects manufactured in a production line. Due to the at least computationally identical alignment referring to the original alignment in the stamper, it is possible to deduce possible defects that were produced during the pressing process by a defective stamper.

It is, in principle, also possible to provide other or additional markings. For example, a marking may be realized in the form of a straight line 22 that is arranged on the inner edge region 14 or on the outer edge region 19. The marking may also be formed by delimited surface sections. It is essential with respect to the design and arrangement of the marking that said marking is not completely rotationally symmetrical and thus allows a defined positioning of the otherwise completely symmetrical object in the rotating direction. Separate markings 23 may also be provided in the lead-out 18 or in the coaxial region 15 of the ID code 16. Markings of this type can also be produced by the stamper, i.e., an unequivocal allocation and alignment of the CD is possible.

Such a method allows, in particular, the recognition and classification of stamper defects. In this case, it is possible to carry out the examination in such a way that stamper defects that do not yet result in refuse are accepted. These still harmless defects can be correspondingly monitored. It is also possible to terminate this defect suppression, e.g., if it is determined that the defect is merely temporary because it was caused by slight soiling of the stamper and the ensuing data carriers no longer contain this defect. Consequently, the examination and inspection of the data carriers can be additionally fine-tuned.

This pertains, in particular, to a precise position such that other defects that, for example, lie on the same radius, can still be detected. It is also possible to detect stamper defects in a timely fashion such that a stamper can be correspondingly replaced without producing refuse with the stamper.

What is claimed is:

1. A method for optically examining a series of objects that are symmetrical in reference to a rotational axis during or after a manufacturing process of the objects, comprising the steps of:
   providing at least some of the objects with at least one marking (16, 20, 22, 23), said marking making it possible to unequivocally determine an angular position of each object about a rotational axis (13) relative to said marking on objects manufactured in the same manufacturing process;
   scanning at least one section of the objects with at least one scanning element such that said marking is detectable;
   displaying on a display element a scanned result of geometric regions (21) in the same angular position relative to the marking with corresponding positions on other objects relative to the marking; and
   evaluating with an evaluation means the defects of the respective objects which have at least approximately a same position in reference to the angular position relative to the marking and a same radial distance from the rotational axis with criteria other than stochastically occurring defects.

2. A method according to claim 1, wherein said evaluation means counts defects that always occur at approximately the same position on the respective objects, and wherein a signal is generated if a predetermined number of identical defects with approximately the same position on the respective objects is exceeded.

3. A method according to claim 1, wherein said evaluation means recognizes defects that always occur at approximately the same position on the respective objects and generates a corresponding signal even if such a defect does not result in refuse in individual instances.

4. A method according to claim 1, wherein said evaluation means recognizes defects that always occur at approximately the same position on the respective objects, and wherein these positions can be declared as being defect-free such that harmless system defects that are detected do not result in refuse.

5. A method according to claim 4, wherein the regions which were declared to be defect-free are monitored, and wherein a signal is generated if the defect changes, in particular, with respect to its size.

6. A method according to claims 1, wherein said marking is always situated in the same position on the display means so as to always illustrate the objects in an identical alignment.

7. A method according to claim 1, wherein said object is a circular data carrier and wherein said marking forms at least a part (16, 20) of an ID code of said data carrier.

8. A method according to claim 1, wherein said objects are circular data carriers manufactured by means of pressing, and wherein said marking (22, 23) is applied after the pressing of a blank, namely in such a way that the angular position of the blank relative to its angular position in the stamper can be unequivocally defined.

9. A method according to claim 1, wherein said marking (22, 23) is applied onto the object in a removable fashion.

10. A device for optically examining a series of objects that are symmetrical in reference to a rotational axis during or after the manufacturing process of the objects, comprising:
    at least one optical scanning element that scans at least a part of the objects which have at least one marking (16, 20, 22, 23), said marking making it possible to unequivocally determine an angular position of each object about the rotational axis (13) relative to the marking for objects manufactured in the same manufacturing process;
    an examination unit that evaluates and displays on a display element a result of the scanning of geometric regions (21) with corresponding positions on the objects in reference to the marking in the same angular position in reference to the marking;
    at least one memory for storing at least the defects and their unequivocal positional data of a predetermined number of successively examined objects; and
    at least one evaluation element that evaluates the defects of the respective objects in approximately the same position in reference to the angular position of the marking and with the same radial distance from the rotational axis with criteria other than stochastically occurring defects.

11. A device according to claim 10, wherein the objects are circular data carriers.

* * * * *